United States Patent
Baum

Patent Number: 5,100,319
Date of Patent: Mar. 31, 1992

[54] SUBGINGIVAL DELIVERY TIP

[75] Inventor: John W. Baum, Fort Collins, Colo.

[73] Assignee: Teledyne Industries, Inc., Fort Collins, Colo.

[21] Appl. No.: 445,380

[22] Filed: Dec. 4, 1989

[51] Int. Cl.⁵ .............................................. A61H 9/00
[52] U.S. Cl. .................................. 433/80; 128/62 A; 128/66
[58] Field of Search .......................... 433/80, 88, 147; 128/62 A, 66; 222/567, 569, 570

[56] References Cited

U.S. PATENT DOCUMENTS

| | | | |
|---|---|---|---|
| 1,961,489 | 6/1934 | Hein | 128/66 X |
| 2,514,576 | 7/1950 | Hein et al. | 128/62 A X |
| 2,641,839 | 6/1953 | Black | 433/88 |
| 2,733,713 | 2/1956 | Kabnick | 128/62 A |
| 3,199,510 | 8/1965 | Sinai | 128/62 A |
| 3,393,673 | 7/1968 | Mattingly | 128/66 X |
| 3,736,923 | 6/1973 | Parkison | 128/66 |
| 3,847,145 | 11/1974 | Grossan | 128/66 |
| 4,365,752 | 12/1982 | Waisbren et al. | 128/66 X |
| 4,416,628 | 11/1983 | Cammack et al. | 433/80 |
| 4,787,845 | 11/1988 | Valentine | 433/88 |
| 4,906,187 | 3/1990 | Amadera | 128/66 X |

FOREIGN PATENT DOCUMENTS 1491090 2/1969 Fed. Rep. of Germany ........ 433/88

*Primary Examiner*—Robert P. Swiatek
*Assistant Examiner*—Todd E. Manahan
*Attorney, Agent, or Firm*—Hugh H. Drake

[57] ABSTRACT

For use with an oral irrigating appliance which provides a series of pulses of fluid through a flexible hose to a user-held handle, a subgingival delivery tip is in the form of an elongated hollow shank with a knob at one end thereof. Formed at the other end of the shank is an in-turned constriction which defines a passage more narrow than the inner width of the shank. A probe of resilient material has an outer cone-shaped portion projecting away from and with its base seated adjacent to the outer end of the constriction. That probe also has a necked-down central portion continuing centrally from its base through the passage and continuing into an enlarged button-shaped inner portion on the inner end of that central portion with that inner portion being received within the shank in a position seated adjacent to the innermost end of the passage. A channel is pierced centrally through the entirety of all of the different portions of the probe.

2 Claims, 3 Drawing Sheets

SUBGINGIVAL DELIVERY TIP

The present invention pertains to a subgingival delivery tip. More particularly, it relates to a tip structure devised for use on irrigating appliances which supply pulses of fluid through the tip to enable the delivery of solutions to the subgingival areas within the mouth of the user.

Various devices have been developed for the purpose of assisting in the cleaning of the teeth and their surroundings. U.S. Pat. No. 3,199,510 to Sinai employed a squeeze bottle with a cone-shaped spout which enabled the user to pulsate delivery of water toward the area of the teeth. U.S. Pat. No. 2,514,576 to Hein et al pertained to a hand-held syringe which could be used for similar purposes. A related patent disclosure was U.S. Pat. No. 1,961,489 to Hein.

A number of patents have issued with respect to oral hygiene appliances which produce a series of water pulses for delivery into the mouth of the user by what often was called a "jet tip" mounted on a handle and connected to the appliance by a flexible hose. Exemplary are U.S. Pat. No. 3,393,673 to Mattingly and U.S. Pat. No. 4,416,628 to Cammack et al.

The aforementioned patents all had a general purpose of directing pulses of the water against the teeth for cleaning purposes. At least some of them emphasized also the desirable effect of a massage action on the gums. Further attention to tooth care led to a modification of the hand-operated jet tip to include at its outer end a resilient probe having a water channel through its interior and designed to enable it to penetrate beneath the gum line in between the gums and the lower portions of the teeth. That generally successful device is shown in U.S. Pat. No. Des. 304,231, issued Oct. 24, 1989.

The device of the present invention represents the results of further research and development in order to extend the benefits of the device of that last-mentioned patent in terms of both efficacy of action and facility of manufacure.

Related to that general objective is the provision of a probe formation captivation which ensures integrity of the relationships between the parts during continued usage.

In accordance with the present invention, a subgingival delivery tip has an elongated hollow shank with a knob at one end thereof. An in-turned constriction is formed at the other end of the shank to define a passage more narrow than the inner width of the shank. A probe of resilient material has an outer cone-shaped portion projecting away from and with its base seated adjacent to the outer end of the constriction. A necked-down central portion of the probe continues centrally from its base through that passage, and an enlarged button-shaped inner portion is received within the shank in a position seated adjacent to the inner end of the passage. A channel is pierced centrally through the entirety of all of those portions.

The features of the present invention which are believed to be patentable are set forth with particularity in the appended claims. The organization and manner of operation of one specific embodiment of the invention, together with further objects and advantages thereof, may best be understood by reference to the following description taken in connection with the accompanying drawings, in the several figures of which like reference numerals identify like elements and in which:

Figure 1:
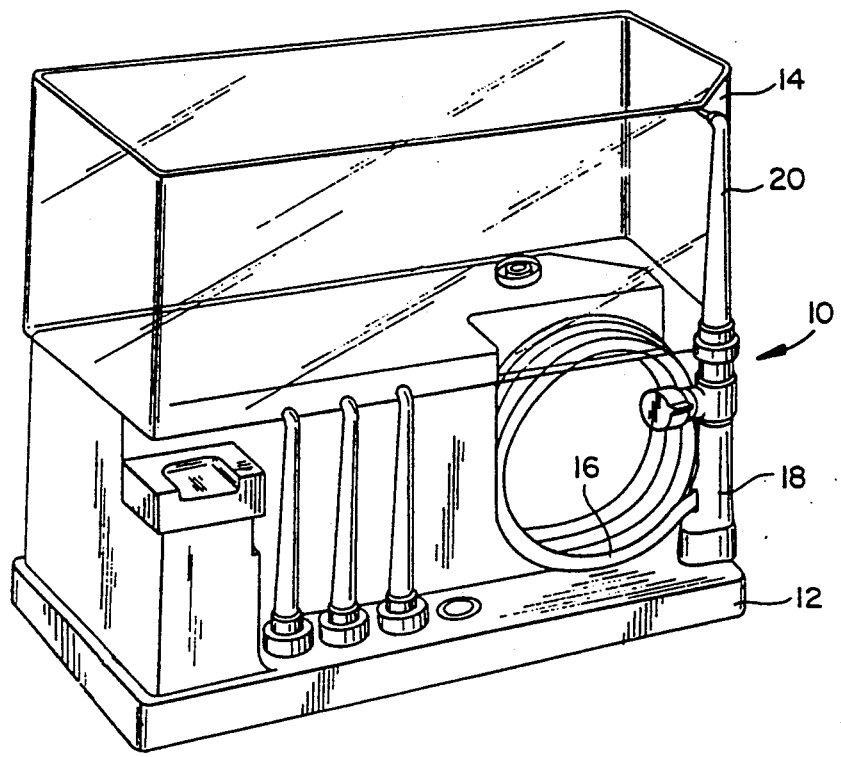
FIG. 1 is an isometric generally-front view showing an overall arrangement of an oral hygiene appliance which utilizes a subgingival delivery tip.
Figure 2:
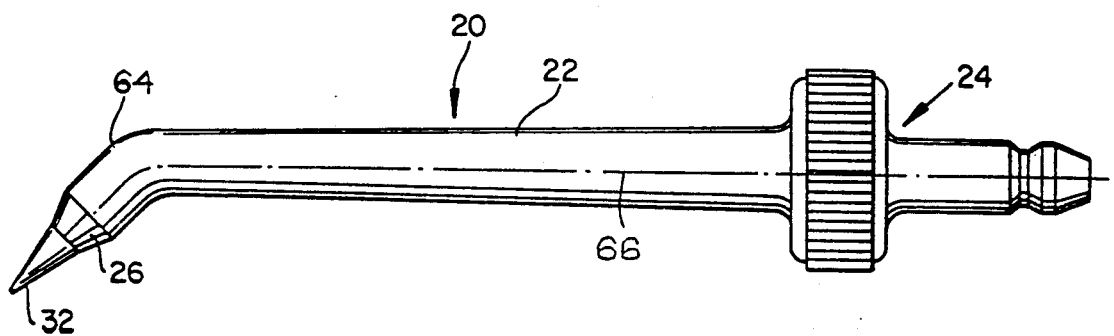
FIG. 2 is a side elevational view of a subgingival delivery tip shown in FIG. 1.
Figure 3:
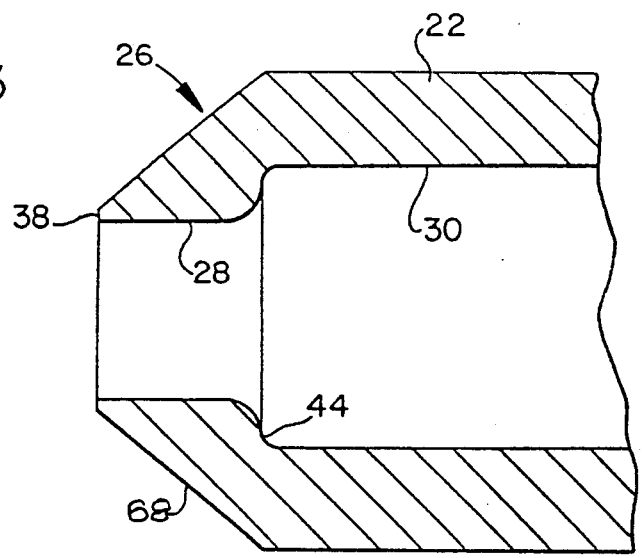
FIG. 3 is a fragmentary longitudinal cross-sectional view of a portion of the tip of FIG. 2.
Figure 4:
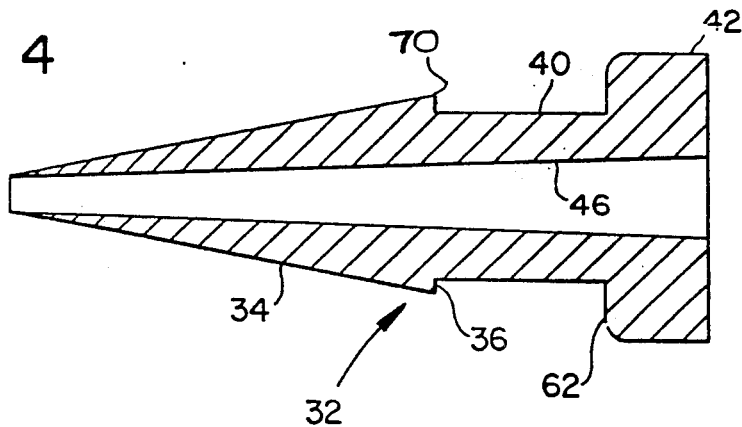
FIG. 4 is a longitudinal cross-sectional view of a resilient probe used in the tip of FIG. 3.
Figure 5:
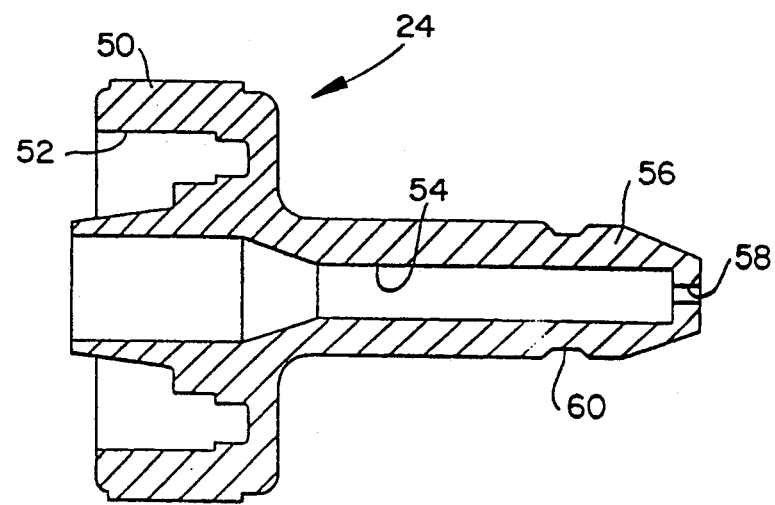
FIG. 5 is a longitudinal cross-sectional view of a base or knob employed in the tip shown in FIG. 2.
Figure 6:
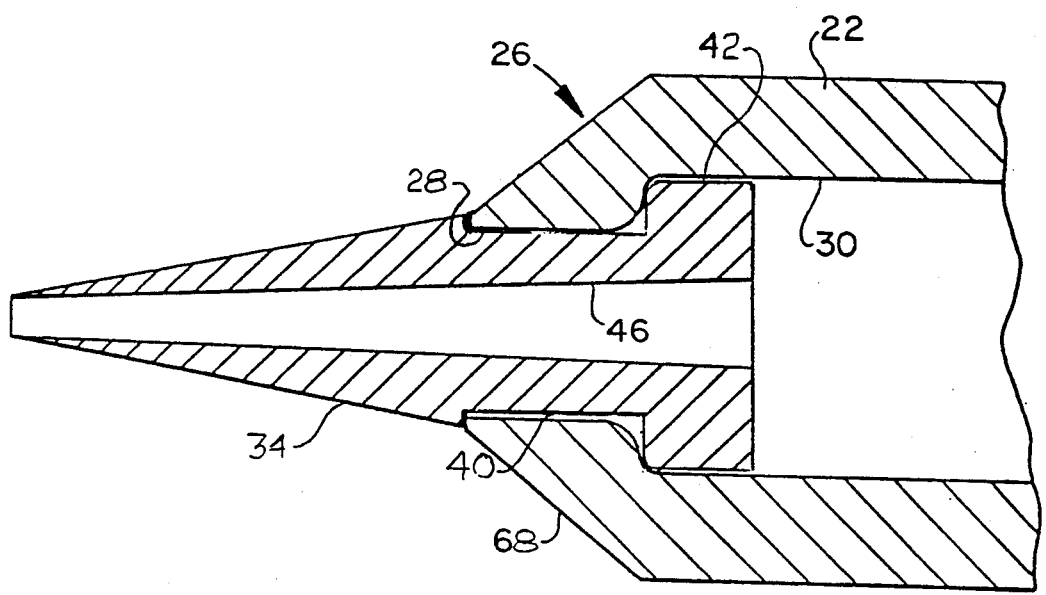
FIG. 6 is a longitudinal cross-sectional view of the components shown in FIGS. 3 and 4 as assembled together.

An oral hygiene device 10 has a platform 12 which is a lower part of a housing from which upstands a reservoir 14 that in use contains water or other liquid to be discussed further hereinafter. Leading outwardly from that housing is a flexible hose 16 on the remote end of which is a handle 18 into which is plugged a jet tip 20.

As such, the overall arrangement shown in FIG. 1 is that of the oral hygiene appliance of co-pending U.S. patent application Ser. No. 875,203, filed June 17, 1986 and as it appears ready for use with its reservoir upstanding as compared with a storge position when the reservoir is oriented dto ensleeve the upper or main housing portion on the platform. For background as to the other features and operation of the oral hygiene appliance itself, that latter application is incorporated herein by reference as to form a part hereof. It will suffice for the present to say that a series of pulses of the water or mixture stored within reservoir 14 is delivered through hose 16 and thereon through jet tip 20. The user may then insert the end of the jet tip into his mouth and direct a pulsating fluid flow to the desired subgingival area between his teeth and gums.

Jet tip 20 includes an elongated hollow shank 22 with a knob 24 at one end thereof. An in-turned constriction 26 is formed at the other end of shank 22 to define a passage 28 more narrow than the width of the internal wall 30 of shank 22. A probe 32 of resilient material has an outer cone-shaped portion 34 projecting away from and with its base 36 seated adjacent to the outer end 38 of constriction 26.

A necked-down central portion 40 of probe 32 continues centrally from base 36 through passage 28. An enlarged button-shaped inner portion 42 of probe 32 on the inner end of central portion 40 is received within shank 22 in a position seated adjacent to the shoulder 44 at the inner end of passage 28. A channel 46 is pierced centrally through the entirety of all of portions 34, 40 and 42.

Knob 24 includes an exteriorly-knurled annulus 50 having a forwardly defined recess 52 into which that end of shank 22 is received and sealed as by ultrasonic welding. Leading through the interior of knob 24 is a conduit 54 with the knob terminating at its end away from shank 22 in a plug 56. Conduit 54 leads to an orifice 58 which communicates with hose 16 to receive the pulsating delivery of fluid. As will be seen, plug 56 includes a circumferential notch 60 which cooperates with an O-ring or the like in handle 18.

The central portion 40 of probe 32 is installed within constriction 26. A seal is effected between the outer peripheral surface of button 42 and internal wall 30 of shank 22. The outward face 62 may also seal against shoulder 44.

The preferred embodiment includes a bending of the outer end portion of shank 22 such that its outer-end seqment 64 is bent away from the longitudinal axis 66 of the remainer of shank 22 in order to point probe 32 to one side at an acute angle to axis 66. As finally assembled into the preferred arrangement, the constricting wall portion 68 of shank 22 merges its exterior wall into substantial alignment with the periphery 70 of base 36 and with channel 46 being defined within that laterally-bent portion.

In a working embodiment, orifice 58 has a nominal diameter of 0.020 inch. The remainder of the passageway defined within knob 24 and shank 22 is larger than that. In the downstream direction, channel 46 tapers from an entrance diameter of 0.050 inch to a minimally larger final apex diameter nominally of 0.022 inch. The larger intermediate diameter allows for accommodation of inlet flow when the outer end of channel 46 is temporarily blocked as by engagement against gum tissue. On the other hand, the gradual constriction imposed by that taper in channel 46 serves to restore substantial balance as between inlet and outlet pressures through the jet tip. At the same time, the ultimate delivery pressure is lowered by orifice 58 to meet the requirements of subgingival delivery as compared with tooth scrubbing and external gum massage.

In operation, the user grasps handle 18 and knob 24 of jet tip 20 in order to direct the pulsating stream of liquid into his mouth and against the teeth and gums. Proceeding further with this particular form of jet tip, the user inserts probe 32 into the pocket between the inner surface of the gum and the wall of the tooth. This permits the delivery of the fluid into the subgingival space.

The fluid used for delivery to the subgingival areas may be only plain water. Often, however, it should be a solution with one or more additives that enhance treatment for specific problems. When treatment is contemplated, much less reservoir capacity than that typical for conventional irrigation of the teeth and gums may be needed. Accordingly, it may be preferable to the user that an appliance such as that shown in FIG. 1 be supplied with an alternate reservoir much smaller than reservoir 14 as illustrated herein. Yet, the reservoir there shown would be used for conventional tooth scrubbing and gum massage.

In the latter connection, it may be noted in FIG. 1 that stored on platform 12 are three additional jet tips which basically look to be the same as tip 20. However, they do not have probe 32 and their internal flow passageway is larger so as better to serve the functions of tooth cleaning and external gum massage wherein the larger reservoir shown becomes preferable. Nevertheless, that larger reservoir still may be used with the subgingival tip to which this application is directed.

Use of the present subgingival probe is not at all limited to use with the cross-referenced patent which is employed herein only for illustrative purposes. Although not as preferred by applicant, the new probe and tip also finds use with an appliance which delivers a continuous stream of fluid. As shown and as preferred, shank 22, probe 32, knob 24 and plug 56 all have a generally circular exterior shape, and the interior passageway and channel all are of cylindrical cross section. Any of those shapes may, if desired, be of something else such as polygonal.

While a particular embodiment of the invention has been shown and described, and certain alternatives and modifications have been taught, it will be obvious to those skilled in the art that changes and modifications may be made without departing from the invention in its broader aspects. Therefore, the aim in the appended claims to cover all such changes and modifications as fall within the true spirit and scope of that which is patentable.

I claim:

1. A subgingival irrigation delivery tip comprising;
   an elongated hollow shank with a knob at one end portion thereof, said hollow shank having an inner width;
   an in-turned constriction formed in the other end portion of said shank to define a passage more narrow than said inner width of said shank, said passage having an inner end and an outer end;
   a probe of resilient material having an outer cone-shaped portion projecting away from and with its base seated adjacent to said other end of said passage, a necked-down central portion of said probe having an inner end and an outer end and continuing centrally from said base through said passage, and an enlarged button-shaped inner end portion of said probe on said inner end of said central portion and received within said shank in a position seated adjacent to said inner end of said passage, with a channel pierced centrally through the entirety of all of said portions of said probe and with said channel having an outlet end and said knob including a fluid-flow orifice of a size approximately the same as that at said outlet end of said channel.

2. A tip as defined in claim 1 in which said outlet end of said channel is minimally larger than the size of said orifice.

* * * * *